United States Patent [19]

Hess

[11] 3,935,213

[45] Jan. 27, 1976

[54] PROCESS FOR HYPOTENSIVE 4-AMINO-2-(PIPERAZIN-1-YL) QUINAZOLINE DERIVATIVES

[75] Inventor: Hans-Jurgen E. Hess, Old Lyme, Conn.

[73] Assignee: Pfizer Inc., New York, N.Y.

[22] Filed: Dec. 5, 1973

[21] Appl. No.: 421,992

[52] U.S. Cl. .................. 260/256.4 Q; 260/268 R; 260/268 CN; 260/268 C; 260/268 FT; 260/564 R; 260/568
[51] Int. Cl.² ............................ C07D 239/08
[58] Field of Search .................. 260/256.4 Q

[56] References Cited
UNITED STATES PATENTS
3,511,836  5/1970  Hess ........................ 260/251 Q Primary Examiner—Nicholas S. Rizzo
Assistant Examiner—David E. Wheeler
Attorney, Agent, or Firm—Connolly and Hutz

[57] ABSTRACT

6,7-Dimethoxy-4-amino-2-(4-substituted piperazin-1-yl)-quinazolines and 6,7,8-trimethoxy-4-amino-2-(4-substituted piperazin-1-yl)quinazolines are produced by either: (1) reaction of the appropriate 4,5-dimethoxy substituted or 3,4,5-trimethoxy substituted 2-aminobenzonitrile with certain 1,4-disubstituted piperazines; or (2) reaction of the appropriate 4,5-dimethoxy substituted or 3,4,5-trimethoxy substituted 2-aminobenzamidine with the same 1,4-disubstituted piperazines. The products are known hypotensive agents.

17 Claims, No Drawings

PROCESS FOR HYPOTENSIVE 4-AMINO-2-(PIPERAZIN-1-YL) QUINAZOLINE DERIVATIVES

BACKGROUND OF THE INVENTION

1. Field of the Invention

This invention relates to a new chemical process for the production of certain known chemical compounds, valuable in the art by virtue of their ability to lower blood pressure in hypertensive mammals. More specifically, these hypotensive agents are 6,7-dimethoxy-4-amino-2-(4-substituted piperazin-1-yl)quinazolines and 6,7,8-trimethoxy-4-amino-2-(4-substituted piperazin-1-yl)quinazolines, use of which is taught in U.S. Pat. Nos. 3,511,836 and 3,669,968.

2. Description of the Prior Art

U.S. Pat. No. 3,511,836 discloses several processes for the preparation of 6,7-dimethoxy-4-amino-2-(4-substituted piperazin-1-yl)-quinazolines. For example, according to the said patent, they can be prepared by reaction of 6,7-dimethoxy-4-amino-2-chloroquinazoline with the appropriate 1-monosubstituted piperazine, or, alternatively, by reaction of either 4,5-dimethoxy-2-aminobenzonitrile or 4,5-dimethoxy-2-aminobenzamidine with the appropriate 1-amidino-4-substituted piperazine. U.S. Pat. No. 3,669,968 teaches the preparation of 6,7,8-trimethoxy-4-amino-2-(4-substituted piperazin-1-yl)quinazolines via reaction of 6,7,8-trimethoxy-4-amino-2-chloroquinazoline with the appropriate 1-monosubstituted piperazine. In Netherlands Pat. No. 7206067, there is disclosed a process which comprises reacting certain o-aminobenzonitriles with cyanamides to produce 2,4-diaminoquinazoline derivatives.

SUMMARY OF THE INVENTION

It is an object of this invention to provide a new process for the preparation of quinazoline compounds of formula which comprises reacting a compound of formula

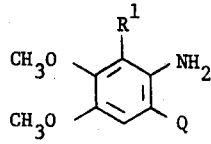

II or a salt thereof, with a compound of formula

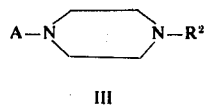

III or a salt thereof, in a reaction-inert, organic solvent; wherein $R^1$ is selected from the group consisting of hydrogen and methoxy;

$R^2$ is selected from the group consisting of alkenyl having from 3 to 5 carbon atoms, benzoyl, furoyl, thienylcarbonyl, alkoxycarbonyl having from 2 to 5 carbon atoms, alkenyloxycarbonyl having from 4 to 5 carbon atoms and (2-hydroxyalkoxy)carbonyl having from 4 to 5 carbon atoms;

Q is selected from the group consisting of cyano and $-C(=NH)-NH_2$;

and A is selected from the group consisting of cyano and $-C(=NH)-X-R^3$, wherein X is selected from the group consisting of O and S, and $R^3$ is alkyl having from 1 to 6 carbon atoms;

provided that when Q is cyano, A is $-C(=NH)-X-R^3$.

A particularly desirable variation of the instant process, as regards the availability of starting materials, and ease of operation, is that embodiment wherein Q is cyano and A is $-C(=NH)-X-R^3$. Preferred examples of $R^3$ are alkyl groups which correspond to the alkyl moiety of readily-available alkanols, such as, for example, methanol, ethanol and isopropanol. Whereas the instant process is useful for the preparation of the said, unknown, hypotensive agents of formula I, it is especially useful in the preparation of two particularly valuable members of this group of congeners; namely, 6,7-dimethoxy-4-amino-2-[4-(2-furoyl)piperazin-1-yl]quinazoline and 6,7,8-trimethoxy-4-amino-2-[4-(2-hydroxy-2-methylprop-1-yloxycarbonyl)piperazin-1-yl]quinazoline, known in the art as prazosin and trimazosin. 6,7,8-Trimethoxy-4-amino-2-[2-methylprop-2-enyloxy-carbonyl)piperazin-1-yl]quinazoline is a valuable starting material for production of trimazosin (U.S. Pat. No. 3,669,968). Prazosin and trimazosin have recently been reported to have therapeutic utility in man (Cohen, Journal of Clinical Pharmacology, 10, 408 [1970]; De Guia, et al., Current Therapeutic Research, 15, 339 [1973]).

DETAILED DESCRIPTION OF THE INVENTION

As indicated before, the object of the instant invention is to provide a process for the preparation of compounds of formula I, by reaction of a compound of formula II, or a salt thereof, with a compound of formula III, or a salt thereof. The reaction is carried out by heating together the starting reagents in an appropriate, reaction-inert, organic solvent, optionally in the presence of a basic catalyst. An appropriate solvent is one which will serve to dissolve at least one of the reactants, and will not adversely interact with either of the starting reagents, or the product. Examples of such solvents are lower alkanols, such as methanol, ethanol, isopropanol and butanol; ethers, such as diethyl ether, tetrahydrofuran, dioxan and 1,2-dimethoxyethane; aromatic hydrocarbons, such as benzene, toluene and xylene; tertiary amides such as N,N-dimethylformamide, N,N-dimethylacetamide and N-methylpyrrolidone; dimethylsulfoxide; and pyridine. The reaction can be carried out over a wide range of temperature, but temperatures in the range from about 50° to about 180°C. are commonly used, and a particularly convenient temperature range is from about 80° to about 130°C. The reaction time needed for the instant process varies according to several factors, such as, for example, the reaction temperature, the reactivity of the starting reagents and the concentrations of the reactants. As will be appreciated by the skilled artist, at lower temperatures longer periods are needed, while at higher temperatures the reaction is complete in a shorter time. In any event, reaction times of several hours, for example, from about 2 hours to about 24 hours, are commonly used.

Although the starting reagents are normally contacted in equimolar proportions, this is not essential to the success of the reaction, and an excess of either reagent can be present.

The quinazoline derivatives of formula I produced in the instant process are recovered from the reaction medium by methods well known in the art. For example, if the product precipitates during the course of the reaction, it can be recovered simply by filtration. Alternatively, when the product does not precipitate spontaneously, it can often be induced to precipitate at the end of the reaction by dilution of the reaction medium with a nonsolvent, such as hexane or water. A further method of product recovery involves removal of the solvents by evaporation, followed by partitioning of the crude product thus obtained between water and a water-immiscible organic solvent. After separation of the two phases, the product-containing phase is evaporated, to yield the product.

As will be realized by the skilled artist, the compounds of formula III, wherein A is —C(=NH)—X—$R^3$, have basic properties, and they will form acid-addition salts. For example, they will form acid-addition salts with such acids as hydrohalic acids, for example, hydrogen chloride and hydrogen bromide, sulfonic acids, for example, methanesulfonic acid, benzenesulfonic acid and p-toluenesulfonic acid, and certain alkanoic acids, for example, trifluoroacetic acid and trichloroacetic acid. Moreover, the acid-addition salts of the said compounds of formulae II and III can successfully serve as starting reagents in the process for the production of the quinazoline compounds of formula I. Thus, in the reaction of a compound of formula I with a compound of formula II, either or both of the starting reagents can be used in the form of its free base, or its acid-addition salt, and this successfully leads to the formation of the corresponding compound of formula I.

However, from a standpoint of speeding up the rate of reaction between a compound of formula II and a compound of formula III, and also of obtaining a good yield of product, it is desirable to carry out the reaction in the presence of a basic catalyst. In this case, it is usual to carry out the reaction in the presence of from 0.5 molar equivalents to about five molar equivalents of a basic catalyst, and preferably in the presence of about one molar equivalent of a basic catalyst. However, even larger amounts of catalyst, for example, up to about 10 molar equivalents, are sometimes used. As will be appreciated by one skilled in the art, if one of the starting reagents is used in the form of its acid-addition salt, one molar equivalent of added basic catalyst is consumed in neutralizing the said acid-addition salt. Consequently, in this case, it is necessary to add to the reaction medium at least two molar equivalents of basic catalyst in order to have 1 molar equivalent of basic agent available to catalyze the reaction. Analogously, when both of the starting reagents are used in the form of their acid-addition salts, it is desirable to add to the reaction medium at least 3 molar equivalents of basic catalyst.

A wide variety of basic catalysts can be used in the present process, such as organic tertiary amines, for example, triethylamine, tributylamine, N,N-dimethylaniline, N-methylmorpholine, pyridine and quinoline; metal hydrides, for example, sodium hydride, potassium hydride and calcium hydride; metal alkoxides, such as sodium methoxide, potassium methoxide and sodium ethoxide; metal alkyls, for example, methyllithium and phenyllithium; and metal salts of amines, for example, lithium isopropylamide.

It will be realized that not all the conditions given above are equally effective or convenient in all cases for the reaction of a compound of formula II with a compound of formula III. Thus the skilled artist will make a selection of appropriate reaction conditions in each case, based on such factors as the stability and reactivity of the starting reagents and the product, the scale of the reaction contemplated, the availability of starting reagents and the ease of isolating the particular product. In particular, the skilled artist will ensure the compatibility of the solvent and basic catalyst chosen, and also ensure that starting reagents and products are not exposed to conditions which would lead to their decompostion.

A variation which is used in some instances for the operation of the process of the instant invention is a method which comprises the steps of: (1) contacting the starting reagents, or acid-addition salts thereof, in a solvent such as those delineated hereinbefore, for a few hours; and then (2) adding to the on-going reaction an appropriate quantity of a basic catalyst, to complete the conversion to quinazoline.

The starting reagent of formula II, wherein $R^1$ is hydrogen and Q is cyano, namely, 2-amino-4,5-dimethoxybenzonitrile, is prepared from 3,4-dimethoxybenzonitrile by nitration followed by reduction with stannous chloride, as taught by McKee, McKee and Bost, Journal of the American Chemical Society, 68, 1902 (1946), and references cited therein. The starting reagent of formula II, wherein $R^1$ is methoxy and Q is cyano, namely, 2-amino-3,4,5-trimethoxybenzonitrile, is prepared in analogous fashion from 3,4,5-trimethoxybenzonitrile, by nitration followed by stannous chloride reduction. Preparation of the starting reagents of formula II, wherein Q is —C(=NH)—$NH_2$, namely 4,5-dimethoxy-2-aminobenzamidine and 3,4,5-trimethoxy-2-aminobenzamidine, is achieved by treating the corresponding compound of formula II, wherein Q is cyano, with hydroxylamine, followed by catalytic hydrogenation, using the method and conditions described by Carrington (Journal of the Chemical Society, London, 2527 [1955]) for the conversion of anthranilonitrile into 2-aminobenzamidine.

The starting reagents of formula III, wherein A is cyano, are prepared by reaction of the appropriate 1-monosubstituted piperazine (IV) with cyanogen bromide;

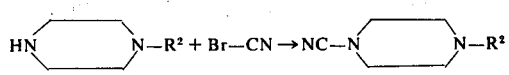

IV

The reaction is carried out by contacting equimolar amounts of the piperazine and cyanogen bromide, according to the method described in Netherlands Pat.

No. 7206067 for the reaction of cyanogen bromide with 1-(2-furoyl)piperazine.

The starting reagents of formula III, wherein A is —C(=NH)—O—R³, are prepared from the corresponding compound of formula III, wherein A is cyano, by reaction with an alkanol of formula R³OH, in the presence of an acid catalyst. The reaction is usually carried out by dissolving equimolar amounts of the starting cyano compound and alkanol in an appropriate aprotic solvent, such as, for example, diethyl ether, tetrahydrofuran, chloroform or methylene chloride, and then saturating the solution with hydrogen chloride at about 0°C. The reaction mixture is then stored at a temperature from about 0°C. to about ambient temperature, for a few hours, for example overnight, and then the product is recovered. In some instances the hydrochloride salt of the product precipitates, in which case it is simply filtered off. In cases where the product does not precipitate, the solvent is removed by evaporation, leaving the hydrochloride salt of the product. The hydrochloride salt can be converted into the free base by conventional means. Other techniques known in the art for the conversion of cyano compounds into imino esters, can also be used for the preparation of the compounds of formula III, wherein A is —C(=NH)—O—R³ (e.g., Shriner and Neuman, Chemical Reviews, 35, 354–358 [1944]).

Preparation of the starting reagents of formula III, wherein A is —C(=NH)—S—R³ can be achieved using the method described above for the preparation of the corresponding compounds of formula III, wherein A is —C(=NH)—O—R³, by replacing the alkanol used therein by the appropriate alkyl mercaptan of formula R³SH. Alternatively, the compounds of formula III, wherein A is —C(=NH)—S—R³ can be prepared from the appropriate 1-monosubstituted piperazine of formula IV, by a two-step procedure which comprises: (1) reaction of the said piperazine derivative with ammonium thiocyanate, and (2) alkylation of the thiocarbamoyl piperazine thus formed with an alkyl halide or alkyl sulfonate of formula R³Y, wherein Y is selected from the group consisting of chloro, bromo, iodo, methanesulfonyloxy, benzenesulfonyloxy and p-toluenesulfonyloxy. The two steps are each carried out in conventional fashion. Techniques for the reaction of amines with ammonium thiocyanate, and for the alkylation of thioureas, are discussed in Houben-Weyl's "Methoden der Organischen Chemie," Volume 9, 1955, pp 887–889 and 900–903.

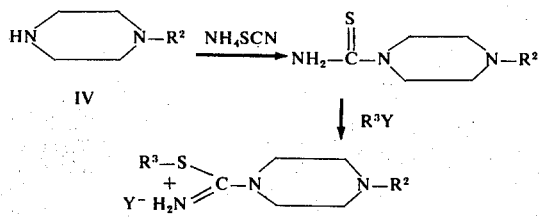

The following Examples are provided solely for the purpose of illustrating the instant invention, and they are not to be construed as imposing any limitations thereon, since many variations are possible without deviating from the spirit or scope thereof.

EXAMPLE I

[Q is CN; A is —C(=NH)—O—C₂H₅]

To a stirred solution of 1.78 g. (0.01 mole) of 4,5-dimethoxy-2-aminobenzonitrile in 30 ml. of N,N-dimethylformamide is added 2.88 g. (0.01 mole) of ethyl 4-(2-furoyl)piperazin-1-ylformimidate hydrochloride, followed by 855 mg. (0.02 mole) of a 56.1% dispersion of sodium hydride in mineral oil. The reaction mixture is stirred at ambient temperature for 30 minutes, and then it is heated to ca. 100°C. and maintained at that temperature for 12 hours. The reaction mixture is cooled to ambient temperature, diluted with an excess of water, and then extracted with chloroform. The chloroform extract is washed several times with water, dried using anhydrous magnesium sulfate, and then evaporated to dryness in vacuo. This affords crude 6,7-dimethoxy-4-amino-2-[4-(2-furoyl)piperazin-1-yl]quinazoline, which is purified further by recrystallization from aqueous ethanol.

EXAMPLE II

When the procedure of Example I is repeated, and the ethyl 4-(2-furoyl)piperazin-1-ylformimidate hydrochloride used therein is replaced by an equimolar amount of:

methyl 4-(2-furoyl)piperazin-1-ylformimidate hydrochloride,
n-propyl 4-(2-furoyl)piperazin-1-ylformimidate hydrochloride,
isobutyl 4-(2-furoyl)piperazin-1-ylformimidate hydrochloride,
isopentyl 4-(2-furoyl)piperazin-1-ylformimidate hydrochloride,
n-hexyl 4-(2-furoyl)piperazin-1-ylformimidate hydrochloride,
methyl 4-(2-furoyl)piperazin-1-ylthioformimidate hydroiodide,
ethyl 4-(2-furoyl)piperazin-1-ylthioformimidate hydrobromide and
isopropyl 4-(2-furyl)piperazin-1-ylthioformamidate hydrobromide,
respectively, the product in each case is 6,7-dimethoxy-4-amino-2-(4-[2-furoyl]-piperazin-1-yl)quinazoline.

EXAMPLE III

The procedure of Example I is repeated, except that the ethyl 4-(2-furoyl)piperazin-1-ylformimidate hydrochloride used therein is replaced by an equimolar amount of:

ethyl 4-allylpiperazin-1-ylformimidate methanesulfonate,
methyl 4-benzoylpiperazin-1-ylformimidate hydrochloride,
isopropyl 4-(3-furoyl)piperazin-1-ylformimidate hydrochloride,
methyl 4-(allyloxycarbonyl)piperazin-1-ylthioformimidate hydroiodide,
ethyl 4-(2-methylprop-2-enyloxycarbonyl)piperazin-1-ylthioformimidate hydrobromide and
ethyl 4-(2-hydroxy-2-methylprop-1-yloxycarbonyl)-piperazin-1-ylthioformimidate hydrobromide, respectively. This affords:

6,7-dimethoxy-4-amino-2-(4-allylpiperazin-1-yl)-quinazoline,
6,7-dimethoxy-4-amino-2-(4-benzoylpiperazin-1-yl)-quinazoline, 6,7-dimethoxy-4-amino-2-[4-(3-furoyl)piperazin-1-yl]-quinazoline, 6,7-dimethoxy-4-amino-2-[4-(allyloxycarbonyl)piperazin-1-yl]quinazoline, 6,7-dimethoxy-4-amino-2-[4-(2-methylprop-2-enyloxycarbonyl)piperazin-1-yl]quinazoline and 6,7-dimethoxy-4-amino-2-[4-(2-hydroxy-2-methylprop-1-yloxycarbonyl)piperazin-1-yl]quinazoline, respectively.

EXAMPLE IV

Following the procedure of Example I, and reacting ethyl 4-(2-hydroxy-2-methylprop-1-yloxycarbonyl)piperazin-1-ylformimidate with 3,4,5-trimethoxy-2-aminobenzonitrile or with 3,4,5-trimethoxy-2-aminobenzamidine, there is produced, in each case, 6,7,8-trimethoxy-4-amino-2-[4-(2-hydroxy-2-methylprop-1-yloxycarbonyl)piperazin-1-yl]quinazoline.

EXAMPLE V

When 4,5-dimethoxy-2-aminobenzamidine hydrochloride reacts with 1-cyano-4-(2-furoyl)piperazine, according to the procedure of Example I, the product is 6,7-dimethoxy-4-amino-2-[4-(2-furoyl)piperazin-1-yl]quinazoline; and when 3,4,5-trimethoxy-2-aminobenzamidine hydrochloride reacts with 1-cyano-4-(2-methylprop-2-enyloxycarbonyl)piperazine, also according to the procedure of Example I, the product is 6,7,8-trimethoxy-4-amino-2-[4-(2-methylprop-2-enyloxycarbonyl)piperazin-1-yl]quinazoline.

EXAMPLE VI

[Q is CN; A is —C(=NH)—O—$C_2H_5$]

To a stirred solution of 3.56 g. (0.02 mole) of 4,5-dimethoxy-2-aminobenzonitrile in 100 ml. of anhydrous benzene is added 20 ml. (0.04 mole) of a 2-molar solution of phenyllithium in 70:30 benzene:ether. The solution is stirred at ambient temperature for 15 minutes and then 5.76 g. (0.02 mole) of ethyl 4-(2-furoyl)-piperazin-1-ylformimidate hydrochloride is added. Approximately 20 ml. of solvent is distilled off, and then the remaining reaction mixture is heated under reflux for 24 hours. The bulk of the solvent is removed by evaporation in vacuo, and then the residue is treated cautiously with 200 ml. of water followed by 200 ml. of chloroform. The chloroform is separated off, and the aqueous phase is re-extracted with chloroform. The combined organic phases are washed with water, dried using anhydrous magnesium sulfate, and then evaporated to dryness in vacuo. This affords crude 6,7-dimethoxy-4-amino-2-[4-(2-furoyl)piperazin-1-yl]quinazoline.

EXAMPLE VII

[Q is CN; A is —C(=NH)—O—$C_2H_5$]

A solution of sodium ethoxide in ethanol is prepared, by dissolving 4.6 g. (0.2 mole) of metallic sodium in 400 ml. of anhydrous ethanol. To this solution is then added 17.8 g. (0.1 mole) of 4,5-dimethoxy-2-aminobenzonitrile, followed by 29.7 g. (0.1 mole) of ethyl 4-furoylpiperazin-1-ylformimidate hydrochloride, at ambient temperature. The mixture is stirred for 15 minutes, and then it is heated under reflux for 16 hours. At the end of that period, the mixture is cooled to 25°C. and the ethanol is almost completely removed in vacuo. Ice-cold water is added to the residue, and the pH is adjusted to ca 6.0 by the addition of dilute hydrochloric acid. The product is filtered off and dried, giving crude 6,7-dimethoxy-4-amino-2-(4-furoylpiperazin-1-yl)-quinazoline.

EXAMPLE VIII

Following the procedure of Example VII, 4,5-dimethoxy-2-aminobenzamidine hydrochloride reacts with 1-cyano-4-allylpiperazine to produce 6,7-dimethoxy-4-amino-2-(4-allylpiperazin-1-yl)quinazoline, and 3,4,5-trimethoxy-2-aminobenzonitrile reacts with methyl 4-(ethoxycarbonyl)piperazin-1-ylthioformimidate hydroiodide to produce 6,7,8-trimethoxy-4-amino-2-[4-(ethoxycarbonyl)piperazin-1-yl]quinazoline.

EXAMPLE IX

[Q is CN; A is —C(=NH)—O—$C_2H_5$]

To a stirred suspension of 3.04 g. of ethyl 4-(2-thienylcarbonyl)-piperazin-1-ylformimidate hydrochloride in 100 ml. of ethyl acetate is added 20 ml. of 40% aqueous potassium carbonate at 0°C. After stirring for a further 15 minutes, the ethyl acetate is removed, dried using anhydrous sodium sulfate, and then concentrated to dryness in vacuo. The residue is redissolved in 40 ml. of N,N-dimethylformamide, and 1.78 g. of 4,5-dimethoxy-2-aminobenzonitrile is added. The solution is maintained at ca 100°C. for 20 hours, and then cooled to around 30°C. The solvent is removed in vacuo at this temperature to yield crude 6,7-dimethoxy-4-amino-2-[4-(2-thienylcarbonyl)piperazin-1-yl]quinazoline.

EXAMPLE X

[Q is CN; A is —C(=NH)—S—$CH_3$]

A solution of 3.56 g. (0.02 mole) of 4,5-dimethoxy-2-aminobenzonitrile and 7.82 g. (0.02 mole) of methyl 4-benzoylpiperazin-1-ylthioformimidate hydroiodide in 100 ml. of n-butanol is heated under reflux for 20 hours. It is then cooled to ambient temperature. The solvent is removed by evaporation in vacuo, leaving crude 6,7-dimethoxy-4-amino-2-(4-benzoylpiperazin-1-yl)quinazoline as its hydroiodide salt.

EXAMPLE XI

When 4,5-dimethoxy-2-aminobenzonitrile and 3,4,5-trimethoxy-2-aminobenzonitrile, respectively, react with 4-(2-furoyl)piperazin-1-ylthioformimidate hydroiodide and 4-(2-methylprop-2-enyloxycarbonyl)piperazin-1-ylthioformimidate hydroiodide, respectively, there is produced:

6,7-dimethoxy-4-amino-2-[4-(2-furoyl)piperazin-1-yl]-quinazoline and 6,7,8-trimethoxy-4-amino-2-[4-(2-methylprop-2-enyloxy-carbonyl)piperazin-1-yl]quinazoline, respectively.

EXAMPLE XII

[Q is CN; A is —C(=NH)—O—$C_2H_5$]

To a stirred solution of 1.78 g. (0.01 mole) of 4,5-dimethoxy-2-aminobenzonitrile in 50 ml. of anhydrous ethanol is added 10 ml. of triethylamine, followed by 2.88 g. (0.01 mole) of ethyl 4-(2-furoyl)piperazin-1-ylformimidate hydrochloride. The reaction mixture is stirred at ambient temperature for 5 hours, and then it is heated under reflux for 12 hours. At this point, all the solvents are removed by evaporation in vacuo, and the residue is triturated under water. The solid is filtered off and dried, yielding crude 6,7-dimethoxy-4-amino-2-[4-(2-furoyl)piperazin-1-yl]quinazoline.

EXAMPLE XIII

[Q is —C(=NH)—NH₂; A is CN]

A solution containing 2.62 g. (0.01 mole) of 3,4,5-trimethoxy-2-aminobenzamidine hydrochloride and 1.83 g. (0.01 mole) of 1-cyano-4-ethoxycarbonylpiperazine in 50 ml. of anhydrous ethanol is stirred at ambient temperature overnight. A 5-ml. aliquot of triethylamine is then added and the reaction mixture is heated under reflux for 12 hours. It is then worked up as described in Example XI, giving 6,7,8-trimethoxy-4-amino-2-[4-ethoxycarbonylpiperazin-1-yl]quinazoline.

What is claimed is:

1. A process for the production of a compound of the formula

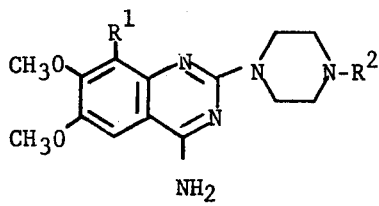

which comprises the steps of reacting a compound of the formula

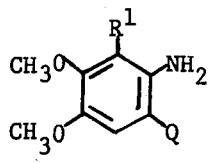

or a salt thereof, with a compound of the formula

or a salt thereof, in a reaction-inert, organic solvent; wherein R¹ is selected from the group consisting of hydrogen and methoxy;

R² is selected from the group consisting of alkenyl having from 3 to 5 carbon atoms, benzoyl, furoyl, thienylcarbonyl, alkoxycarbonyl having from two to five carbon atoms, alkenyloxycarbonyl having from 4 to 5 carbon atoms and (2-hydroxyalkoxy)-carbonyl having from 4 to 5 carbon atoms;

Q is selected from the group consisting of cyano and —C(=NH)—NH₂;

and A is —C(=NH)—X—R³, wherein X is selected from the group consisting of O and S, and R³ is alkyl having from 1 to 6 carbon atoms.

2. The process according to claim 1 wherein Q is cyano.

3. The process according to claim 2 wherein the reaction is carried out at a temperature in the range from about 50° to about 180°C.

4. The process according to claim 3 wherein the reaction is carried out at a temperature in the range from about 80° to about 130°C.

5. The process according to claim 3 wherein the reaction is carried out in the presence of from about 0.5 to about 5 molar equivalents of a basic catalyst.

6. The process according to claim 5 wherein the reaction is carried out in the presence of about 1 molar equivalent of a basic catalyst.

7. The process according to claim 3 wherein R¹ is hydrogen and R² is 2-furoyl.

8. The process according to claim 3 wherein R¹ is methoxy and R² is 2-methyl-2-hydroxyprop-1-yloxycarbonyl.

9. The process according to claim 3 wherein R¹ is methoxy and R² is 2-methylprop-2-enyloxycarbonyl.

10. The process according to claim 1 wherein Q is —C(=NH)—NH₂.

11. The process according to claim 10 wherein the reaction is carried out at a temperature in the range from about 50° to about 180°C.

12. The process according to claim 11 wherein the reaction is carried out at a temperature in the range from about 80° to about 130°C.

13. The process according to claim 11 wherein the reaction is carried out in the presence of from about 0.5 to about 5 molar equivalents of a basic catalyst.

14. The process according to claim 13 wherein the reaction is carried out in the presence of about one molar equivalent of a basic catalyst.

15. The process according to claim 11 wherein R¹ is hydrogen and R² is 2-furoyl.

16. The process according to claim 11 wherein R¹ is methoxy and R² is 2-methyl-2-hydroxyprop-1-yloxycarbonyl.

17. The process according to claim 11 wherein R¹ is methoxy and R² is 2-methylprop-2-enyloxycarbonyl.

* * * * *

UNITED STATES PATENT AND TRADEMARK OFFICE
CERTIFICATE OF CORRECTION

PATENT NO. : 3,935,213
DATED : January 27, 1976
INVENTOR(S) : Hans-Jurgen E. Hess It is certified that error appears in the above-identified patent and that said Letters Patent are hereby corrected as shown below:

Col. 1, between lines 42 and 50, insert the following:

-- 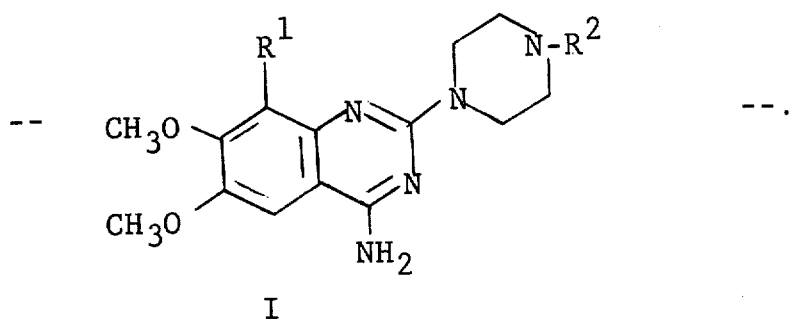 --.

Col. 2, line 27, "unknown" should read -- known --.

Signed and Sealed this

Twentieth Day of July 1976

[SEAL]

Attest:

RUTH C. MASON
Attesting Officer

C. MARSHALL DANN
Commissioner of Patents and Trademarks